(12) United States Patent
Zahniser et al.

(10) Patent No.: US 6,348,325 B1
(45) Date of Patent: *Feb. 19, 2002

(54) CYTOLOGICAL STAIN COMPOSITION

(75) Inventors: David J. Zahniser, Wellesley; Louise M. Isenstein, Carlisle; Norman W. Soule, Brockton; Katherine K. Mui, Chelmsford; Daniel C. Lapen, Lancaster, all of MA (US)

(73) Assignee: Cytyc Corporation, Boxborough, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/430,116

(22) Filed: Oct. 29, 1999

(51) Int. Cl.$^7$ .................................. G01N 1/30
(52) U.S. Cl. ...................................... 435/40.5
(58) Field of Search ....................... 435/40.5

(56) References Cited

U.S. PATENT DOCUMENTS

| | | | |
|---|---|---|---|
| 4,045,655 A | 8/1977 | Suzuki et al. | 435/40.5 |
| 4,175,860 A | 11/1979 | Bacus | 356/39 |
| 4,550,016 A | 10/1985 | Harris | 435/40.5 |
| 4,595,582 A | 6/1986 | Balogh et al. | 435/4 |
| 4,847,910 A | 7/1989 | Sakuraba et al. | 356/39 |
| 4,965,725 A | 10/1990 | Rutenberg | 364/413.1 |
| 4,998,284 A | 3/1991 | Bacus et al. | 382/6 |
| 5,008,185 A | 4/1991 | Bacus | 435/7.23 |
| 5,016,283 A | 5/1991 | Bacus et al. | 435/4 |
| 5,086,476 A | 2/1992 | Bacus | 382/6 |
| 5,109,429 A | 4/1992 | Bacus et al. | 382/6 |
| 5,134,662 A | 7/1992 | Bacus et al. | 382/6 |
| 5,168,066 A | * 12/1992 | Zahniser et al. | 435/40.5 |
| 5,202,931 A | 4/1993 | Bacus | 382/6 |
| 5,252,487 A | 10/1993 | Bacus et al. | 436/63 |
| 5,257,182 A | 10/1993 | Luck et al. | 364/413.1 |
| 5,281,517 A | 1/1994 | Bacus et al. | 435/6 |
| 5,287,272 A | 2/1994 | Rutenberg et al. | 382/15 |
| 5,427,910 A | 6/1995 | Kamentsky et al. | 435/6 |
| 5,473,706 A | 12/1995 | Bacus et al. | 382/100 |
| 5,485,527 A | 1/1996 | Bacus et al. | 382/133 |
| 5,523,207 A | 6/1996 | Kamentsky et al. | 435/6 |
| 5,528,703 A | 6/1996 | Lee | 382/257 |
| 5,541,064 A | 7/1996 | Bacus et al. | 435/6 |
| 5,544,650 A | 8/1996 | Boon et al. | 128/632 |
| 5,566,249 A | 10/1996 | Rosenlof et al. | 382/257 |
| 5,671,288 A | 9/1997 | Wilhem et al. | 356/39 |
| 5,677,762 A | 10/1997 | Ortyn et al. | 382/128 |
| 5,715,327 A | 2/1998 | Wilhem et al. | 382/128 |
| 5,757,954 A | 5/1998 | Kuan et al. | 382/133 |
| 5,781,667 A | 7/1998 | Schmidt et al. | 382/308 |
| 5,787,188 A | 7/1998 | Nelson et al. | 382/133 |
| 5,787,189 A | 7/1998 | Lee et al. | 382/133 |
| 5,793,969 A | 8/1998 | Kamentsky et al. | 382/133 |
| 5,827,680 A | 10/1998 | Meszaros et al. | 435/4 |
| 5,828,776 A | 10/1998 | Lee et al. | 382/133 |
| 5,875,258 A | 2/1999 | Ortyn et al. | 435/7.23 |
| 5,885,840 A | 3/1999 | Kamentsky et al. | 435/63 |
| 5,939,278 A | 8/1999 | Boon et al. | 382/133 |
| 5,942,410 A | 8/1999 | Lam et al. | 435/40.5 |
| 5,987,158 A | 11/1999 | Meyer et al. | 600/476 |
| 5,999,844 A | 12/1999 | Gombrich et al. | 382/133 |
| 6,002,788 A | 12/1999 | Luther | 382/133 |
| 6,026,174 A | 2/2000 | Palcic et al. | 382/133 |
| 6,067,370 A | 5/2000 | Ortyn et al. | 382/133 |

FOREIGN PATENT DOCUMENTS

| | | |
|---|---|---|
| EP | 0 286 255 A2 | 10/1988 |
| EP | 0 445 434 A2 | 9/1991 |

* cited by examiner

Primary Examiner—Louise N. Leary
(74) Attorney, Agent, or Firm—Testa, Hurwitz & Thibeault, LLP

(57) ABSTRACT

The present invention relates to the analysis of cytological material. Specifically, the invention relates to stains and methods of producing the stains, methods of staining cells for cytological or histological analysis to contrast the nuclear portion of the cell from the cytoplasmic portion, and systems and methods for illuminating a cytological sample. The analysis can be automated or manual.

62 Claims, 18 Drawing Sheets

| THIONIN | |
|---|---|
| Lauth's Violet | |
| Aldrich Cat. No. | 86,134-0 |
| Sigma Prod. No. | T3387 |
| Grade | Certified |
| CAS No. | [78338-22-4] |
| C.I. No. | 52000 |
| Mol. Form. | $C_{14}H_{13}N_3O_2S$ |
| F.W. | 287.34 |
| Appearance | Very dark-green powder |
| $\lambda_{max}$ | 598nm in water |
| Solubility | $H_2O$    30mg/ml |
| | EGME    4mg/ml |
| | EtOH    3mg/ml |

| THIONIN | |
|---|---|
| Lauth's Violet | |
| Aldrich Cat. No. | 86,134-0 |
| Sigma Prod. No. | T3387 |
| Grade | Certified |
| CAS No. | [78338-22-4] |
| C.I. No. | 52000 |
| Mol. Form. | $C_{14}H_{13}N_3O_2S$ |
| F.W. | 287.34 |
| Appearance | Very dark-green powder |
| $\lambda_{max}$ | 598nm in water |
| Solubility | $H_2O$ 30mg/ml<br>EGME 4mg/ml<br>EtOH 3mg/ml |

FIG. 1

| | EOSIN Y<br>Acid Red 87 | |
|---|---|---|
| Aldrich Cat. No. | 11,983-0 | 21,612-7 |
| Sigma Prod. No. | E4382 | — |
| Grade | Certified | Indicator |
| Dye content | ~90% | ~80% |
| CAS No. | [548-26-5] | |
| C.I. No. | 45380 | |
| Mol. Form. | $C_{20}H_6Br_4Na_2O_5$ | |
| F.W. | 691.88 | |
| Appearance<br>$\lambda_{max}$ | Rust powder<br>514nm in water + 1ml<br>1% sodium carbonate | Dark red-brown powder<br>517nm in water + 1ml<br>1% sodium carbonate |
| Solubility | $H_2O$ 40mg/ml<br>EGME 40mg/ml<br>EtOH 10mg./ml | 200mg/ml<br>50mg/ml<br>20mg/ml |

FIG. 3

| LIGHT GREEN SF YELLOWISH | |
|---|---|
| Acid Green 5 | |
| Aldrich Cat. No. | 86,120-0 |
| Sigma Prod. No. | L1886 |
| Grade | Certified |
| CAS No. | [5141-20-8] |
| C.I. No. | 42095 |
| Mol. Form. | $C_{37}H_{34}N_2Na_2O_9S_3$ |
| F.W. | 792.86 |
| m.p. | 288°C (dec.) |
| Appearance | Deep-purple powder |
| $\lambda_{max}$ | 630(422)nm in water |
| Solubility | $H_2O$  100mg/ml<br>EGME  100mg/ml<br>EtOH  2mg/ml |

FIG. 4

LED KOEHLER ILLUMINATION SYSTEM

LED FIBER ILLUMINATION SYSTEM

LED MULTICHIP MODULE WITH MICROLENSES

XX
XXX
XX

FIG. 14A

XOX
OXO

FIG. 14B

XOX
OXO
XOX

FIG. 14C

CYTOLOGICAL STAIN COMPOSITION

CROSS-REFERENCE TO RELATED APPLICATIONS

This application incorporates herein by reference three U.S. patent applications filed of even date herewith entitled Cytological Imaging System and Method, Cytological Stain Composition Including Verification Characteristic, and Apparatus and Methods for Verifying the Location of Areas of Interest Within a Sample in an Imaging System, and identified by Attorney Docket Nos. CYM-032, CYM-033, and CYM-034, respectively.

TECHNICAL FIELD

The present invention relates to the analysis of cytological material. Specifically, the invention relates to stains and methods of producing the stains, methods of staining cells for cytological or histological analysis to contrast the nuclear portion of the cell from the cytoplasmic portion, and systems and methods for illuminating a cytological sample. The analysis can be automated or manual.

BACKGROUND INFORMATION

Cytology is the branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "Pap smear" test, in which cells are scraped from a woman's cervix and analyzed in order to detect the presence of abnormal cells, a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions are typically applied to the cells on the glass slide, often called a cell smear, for facilitating examination and for preserving the specimen for archival purposes.

A traditional multicolored stain is desirable for staining cell smears for certain cytological analyses. It is advantageous to stain the nucleus and the cytoplasm of the specimen with different colors, so that the nuclear material and cytoplasmic material can be readily distinguished either visually or by automated imaging equipment. In one staining practice, the cytoplasm is transparent, whereas the nucleus is transparent to opaque. This staining pattern allows the cytologist to distinguish cells which are morphologically abnormal indicated, for example, by nuclear material which is excessively large and/or dark in color. In addition, cytologists find the variety of colors of the traditional stains, particularly the Papanicolaou stain, helpful to reduce eye strain and to aid diagnosis.

Traditional stains, including the Papanicolaou stain, are difficult for an automated system to analyze. The variety of colors in the cytoplasm from traditional stains, which are straightforward for the human eye to distinguish, are not readily analyzed with automated imaging systems because they contrast to varying degrees with the traditional blue hematoxylin stain of the nucleus. The varying contrast makes automated analysis unreliable.

During the approximately seventy years since its introduction, the original Papanicolaou stain has undergone many modifications. Currently, the dyes, reagents, and methodology vary widely based on the preferences of each laboratory. While standardization of a Papanicolaou-like stain has been proposed for many years, there has been little incentive for laboratories to do so. This variability affects current imaging technologies which may reject numerous slides either because of problems inherent with a conventional Pap smear preparation, or because of poor staining that produces nuclearcytoplasmic contrast that is inadequate for image acquisition and analysis.

A number of researchers have developed algorithms in an attempt to attain automated analysis of cells stained with the multicolored Papanicolaou stain. Such techniques involve the use of various instrumental artifacts, such as different colors of light, filters, and color television cameras. Many require a high level of sophistication that is costly in terms of hardware and software. Further, these approaches have not proven accurate and reliable enough to be widely used in clinical cytological and histological diagnoses.

Conventional machine vision illumination sources are low efficiency broadband sources such as tungsten-halogen, sodium-halide, or xenon lamps. These sources convert a small percentage of their input energy to broadband light. Accordingly, efficiency drops significantly in a cytological application that requires a narrow band light source. Typically, these devices generate a significant amount of heat, require filters for obtaining correct wavelengths, and are relatively large.

It is an object of the present invention to provide a stain that creates a high contrast between the nucleus and the cytoplasm of a cell. It is a further object of the invention to stain the cytological material such that the cytoplasm is relatively transparent to an automated machine vision system, but visible to an observer.

It is another object of the invention to provide a stain with a dual peak responsiveness when exposed to two distinct light wavelengths and a system for verifying a specific stain was used based on the dual peak responsiveness.

It is still a further object of the present invention to provide a method of cytological analysis in which the cells are multicolored and the nuclear portion is readily distinguishable from the cytoplasmic portion, both with automated imaging equipment and with human vision analysis.

It is yet another object to provide a method of cytological analysis in which the characteristics of the stained cells can be accurately determined with both manual and automated analysis procedures.

An additional object of the present invention is to provide a system and method for illuminating cytological samples, wherein the illumination is supplied by two different light sources with two different wavelengths. One light source verifies the stain used and the other light source facilitates analysis of the cytological sample.

SUMMARY OF THE INVENTION

Generally, the invention addresses the problems outlined above by means of unique stains, methods of staining cytological material, and illumination systems. Other techniques for addressing some of the drawbacks associated with the traditional Papanicolaou stains are disclosed in U.S. Pat. No. 5,168,066, assigned to the same assignee as the instant application, the disclosure of which is hereby incorporated by reference in its entirety.

In one aspect, the invention relates to a cytological staining solution. The solution includes methanol, phenol, and thionin. In some embodiments, an acid may be present. The acid can be almost any acid traditionally used to adjust the pH of a solution. For example, acetic acid, nitric acid, hydrochloric acid, phosphoric acid, formic acid, sulfuric acid, or citric acid could be used. In various embodiments, the methanol used can be various grades, the phenol source can be loose crystals having an ACS grade of at least about 95%, the thionin can be a certified dye powder, and the acid can be glacial acetic acid of various grades. The ACS grade is an indicator of the purity of the components. Components in accordance with equivalent grading systems are acceptable. In addition, the thionin can be synthesized. In one embodiment, the staining solution has an acidic pH value, preferably about 5–7, and more preferably about 6.70+/−0.05. In one embodiment, the phenol has a weight to volume ratio of about 0.8% to about 1.2%, and preferably about 1.0%. In another embodiment, the thionin has a weight to volume ratio of about 0.2% to about 0.5%, preferably about 0.3% to about 0.4%, and more preferably about 0.345%. The weight to volume ratio, expressed as wt/v, is a measure of the weight of any one component as a percentage of the volume of the entire solution.

In another aspect, the invention relates to a method of producing a staining solution. The method includes the steps of mixing methanol, phenol, and thionin, stirring the mixture, filtering the mixture, and adding an acid to adjust the pH value of the mixture to about 6.7. The acid is preferably added slowly while stirring. As discussed above, the acid can be almost any acid traditionally used to adjust the pH of a solution. In one embodiment, the mixture includes an equivalent ratio of about one liter of methanol, about 10 grams of phenol, and about 3.45 grams of organic or synthetic thionin. The mixture may be filtered using a filter with about a 1–20 micron particle retention. The mixture may be stirred for at least about 1 hour.

In still another aspect, the invention relates to a cytological counterstaining solution. Counterstaining is where the cells are stained with one or more dyes that are primarily taken up by the cytoplasm. The solution includes a reagent alcohol, eosin Y, thionin, and light or fast green SF yellowish. In various embodiments, the reagent alcohol can be 200 proof, the eosin Y, thionin, and light or fast green SF yellowish source can be certified dye powders, and an acid may be present, such as glacial acetic acid, ACS grade 99%. The thionin can be organic or synthetic. In one embodiment, the staining solution has an acidic pH value, preferably about 5–6 and more preferably about 5.50+/−0.05. In another embodiment, the reagent alcohol consists of about 90% ethanol, 5% isoproponal, and about 5% methanol. In one embodiment, the eosin Y has a wt/v ratio of about 0.05% to about 0.1%, preferably about 0.067% to about 0.08%, and more preferably about 0.0721%. In another embodiment, the thionin has wt/v ratio of about 0.01% to about 0.03%, preferably about 0.015% to about 0.025%, and more preferably about 0.0171%. In another embodiment, the light or fast green SF yellowish has a wt/v ratio of about 0.015% to about 0.03% and preferably about 0.0231%.

In yet another aspect, the invention relates to a method of producing a counterstaining solution. The method includes the steps of mixing a reagent alcohol, eosin Y, thionin, and light or fast green SF yellowish, stirring the mixture, filtering the mixture, and adding an acid to adjust the pH value of the mixture to about 5.5. As discussed above, the acid can be almost any acid traditionally used to adjust the pH of a solution. In one embodiment, the mixture includes an equivalent amount of about one liter of reagent alcohol, about 0.721 grams of eosin Y, about 0.171 grams of organic or synthetic thionin, and about 0.231 grams of light or fast green SF yellowish. In other embodiments, the mixture is filtered using a filter with about a 1–20 micron particle retention. The mixture may be stirred for at least about 1 hour.

In still yet another aspect, the invention relates to a method of staining cytological material with a thionin-phenol solution. The thionin-phenol solution binds preferentially to nuclear cytological material relative to cytoplasmic cytological material. The solution can include methanol, phenol, and thionin, and can be about a 0.3% thionin solution. The thionin can be organic or synthetic. In one embodiment, the cytological material is dipped into a salt bath prior to staining. The salt bath can be about a 10% salt solution. In another embodiment, the method includes the step of counterstaining the cytological material after staining with the thionin-phenol solution.

Various embodiments of this aspect of the invention can include the following features. The cytological material can be rinsed or dipped in an alcohol bath prior to counterstaining in a counterstain solution which includes a reagent alcohol, eosin Y, thionin, and light or fast green SF yellowish. The thionin can be organic or synthetic. The counterstaining solution binds preferentially to cytoplasmic cytological material relative to nuclear cytological material. The counterstaining solution can include at least one of the components of the thionin-phenol stain, thionin in one embodiment, such that the thionin substantially replenishes the thionin depleted during the rinsing. At least one of the thionin-phenol solution and the counterstaining solution discernibly stain the cytological material in the visible light range, or both the thionin-phenol solution and the counterstaining solution discernibly stain the cytological material in the visible light range. Additionally, the cytological material can be rinsed or dipped into an alcohol bath after counterstaining.

An additional aspect of the invention relates to counterstaining previously stained material, wherein the counterstain includes a component from the previous stain. The process of counterstaining the previously stained material replenishes any loss of the previous stain component that may have occurred subsequent to the initial staining, for example, through rinsing the material after staining. In one embodiment of this method, the previously stained material is rinsed prior to counterstaining. The rinse can be an alcohol bath.

Another aspect of the invention relates to an optical instrument lighting system that includes a first light source and a second light source. The first light source has a first wavelength, which may be between about 690 nm and about 750 nm. The first light source is used to verify a stain used on a cytological sample. The second light source has a second wavelength different than the first wavelength, and may be between about 500 nm and about 600 nm. The second light source is used to illuminate the cytological sample for viewing. In various embodiments, the first light source can be a red light emitting diode (LED) and the second light source can be a green LED or an array of up to eight or more green LEDs. The light source can operate on low voltage, such as 5 volts DC. LEDs are bright, stable, and available in a very wide range of illumination wavelengths. Furthermore, LEDs efficiently produce a narrow band of illumination (typically 15 nm), eliminating the need for narrow band filters and allowing all energy to be put into the desired illumination wavelength. Conventional illumination such as tungsten-halogen bulbs put out a lot of wasted light and heat when narrow band illumination is desired. LEDs generate significantly less heat and require substantially less power than conventional imaging light sources. In fact, standard light sources are often insufficient to obtain the necessary shutter times. In addition, LEDs are relatively tiny.

A further aspect of the invention relates to an LED array for use with a system for imaging a cytological sample. The LED array includes a red LED for verifying the stained sample was stained with a predetermined stain and a green LED for illuminating the cytological sample for imaging. The array can include up to eight or more green LEDs and can operate on low voltage, such as 5 volts DC.

A still further aspect of the invention relates to a system for imaging a cytological sample including nuclear material and cytoplasmic material. The system includes an optical instrument and first and second light sources, the first light source having a first wavelength for verifying that a specific stain was used on the cytological sample, wherein the specific stain will permit transmission of light at a wavelength of about 720 nm. The second light source has a second wavelength for illuminating the cytological sample for imaging, wherein the stained nucleus of the sample will permit transmission of light at a wavelength of about 570 nm and the cytoplasm will be essentially invisible to the system. In one embodiment, the stain is a thionin-phenol solution, preferably about a 0.3% thionin solution. In another embodiment, the cytoplasm is visible to an observer. In various embodiments, the first light source can be a red LED and the second light source can be a green LED or an array of up to eight or more green LEDs. The light sources can operate on low voltage, such as 5 volts DC.

In yet another aspect, the invention relates to a method of imaging a cell. The method includes the steps of staining the nuclear material of the cell, staining the cytoplasmic material of the cell, illuminating the cell with a first light source has a first wavelength for verifying that a specific stain was used, and illuminating the cell with a second light source having a second wavelength for imaging the nuclear material.

Additional embodiments according to the foregoing aspect of the invention may include the following features. The first wavelength is between about 690 nm and about 750 nm, and the second wavelength is between about 500 nm and about 600 nm. The first light source can be a red LED and the second light source can be a green LED or an array of up to eight or more green LEDs. The light sources can operate on low voltage such as 5 volts DC. The stain used produces a high contrast between the nuclear material and the cytoplasmic material, such that the cytoplasmic material is relatively transparent, or invisible, to an imaging system viewing the cell, but visible to an observer. In particular the nuclear material of the cell may be stained with a thionin-phenol solution, preferably about a 0.3% thionin solution.

In still yet another aspect, the invention relates to a method for verifying that a specific stain was used on a cytological sample. The method includes the steps of staining the cytological sample with a stain having two spectral peaks, at first and second wavelengths, and illuminating the sample with first and second light sources. The first light source has a first wavelength, wherein the specific stain will permit transmission of light at a wavelength of about 720 nm. The second light source has a second wavelength, wherein the specific stain will permit transmission of light at a wavelength of about 570 nm.

Further embodiments according to the foregoing aspect of the invention may include the following features. The first wavelength is between about 690 nm and about 750 nm, and the second wavelength is between about 500 nm and about 600 nm. The first light source can be a red LED and the second light source can be a green LED or an array of up to eight or more green LEDs. The light sources can operate on 5 volts DC. The cytological sample may be stained with a thionin-phenol solution, preferably about a 0.3% thionin solution.

These and other objects, along with advantages and features of the present invention herein disclosed, will become apparent through reference to the following description of embodiments of the invention, the accompanying drawings, and the claims.

BRIEF DESCRIPTION OF THE DRAWINGS

In the drawings, like reference characters generally refer to the same parts throughout the different figures. Also, the drawings are not to scale emphasis instead generally being placed upon illustrating the principles of the invention. Preferred and exemplary embodiments of the present invention are discussed further in the detailed description, with reference to the drawings, which show the following.

FIG. 1 is a chart depicting the characteristics and specifications of a thionin dye.

FIG. 3 is a chart depicting the characteristics and specifications of an eosin Y dye.

FIG. 4 is a chart depicting the characteristics and specifications of a light green SF yellowish dye.

FIG. 14A is a schematic representation of

FIG. 14B is a schematic representation of

FIG. 14C is a schematic representation of

DETAILED DESCRIPTION

Embodiments of the present invention are described below. It is, however, expressly noted that the present invention is not limited to these embodiments, but rather the intention is that modifications that are apparent to the person skilled in the art and equivalents thereof are also included.

One embodiment of the stain is a thionin-phenol solution that includes methanol, phenol, and thionin. The stain may also include an acid for adjusting the pH of the stain solution. The purity of the methanol (methyl alcohol) component can be various grades The phenol component is supplied as loose crystals having an ACS grade purity of at least about 95%. The phenol is a chaotrophic agent available through Aldrich Chemical Company, Inc. of Milwaukee, Wis.; however, an equivalent may be substituted. The thionin component is supplied as a certified dye powder, specifically a BSC-certified, metachromatic, cationic thiazine dye. FIG. 1 depicts the characteristics of one embodiment of the thionin dye used in the present invention as available from Aldrich Chemical Company or SIGMA of St. Louis, Mo.; however, equivalents may be used. The acid for adjusting the pH of the stain can be any one of most common acids, for example, acetic acid, citric acid, nitric acid, hydrochloric acid, phosphoric acid, sulfuric acid, or formic acid.

An acceptable weight per volume (wt/v) ratio of thionin to solution is about 0.2% to about 0.5% wt/v, preferably about 0.3% to about 0.4% wt/v, and more preferably about 0.345% wt/v. The ratio for the phenol is about 0.8% to about 1.2% wt/v and preferably about 1.0% wt/v.

Figure 2:
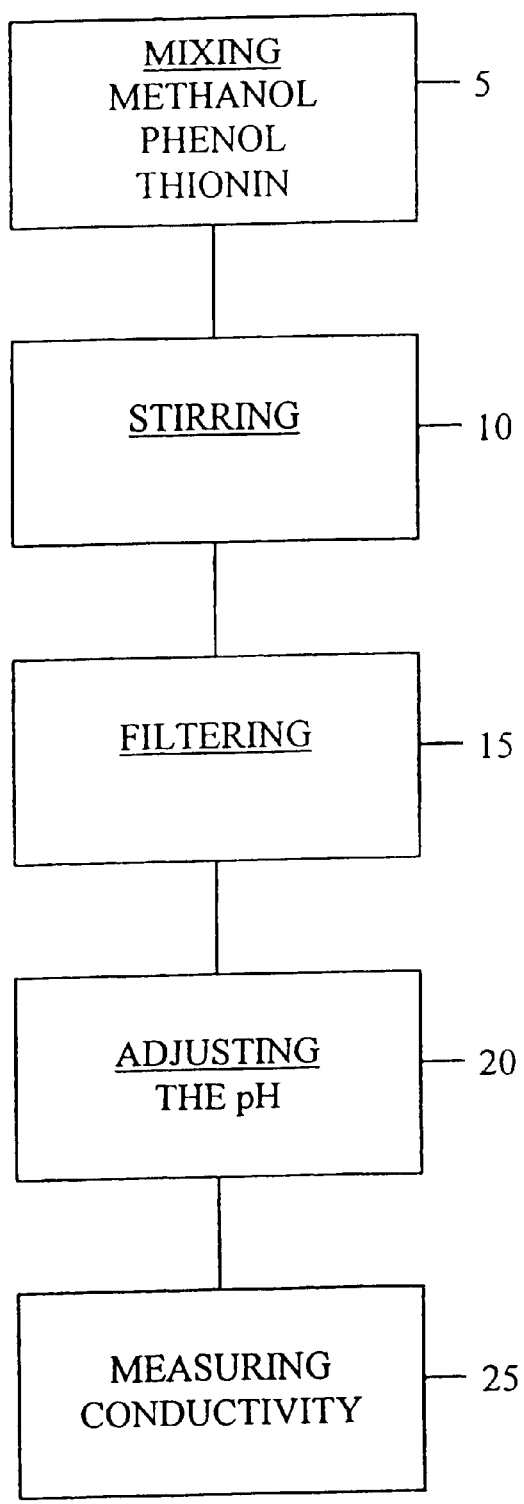
FIG. 2 is a flow chart of one method of producing a thionin-phenol stain.

One method of producing the stain is depicted in FIG. 2. Mixing, step 5, entails adding the phenol crystals and thionin dye to the methanol. Next, the mixture is stirred, step 10, optionally vigorously for up to 15 hours. The mixture is then filtered, step 15. The mixture may be gravity filtered through a filter with about a 1–20 micron particle retention and preferably about 2 micron. One example is no. 4 filter paper as available from Whatmann. Finally, the pH level of the mixture is adjusted, step 20, by adding acid to the solution. The mixture may be stirred continuously while adding the acid. The pH is then adjusted to about 5–7 and preferably about 6.7+/−0.05. Alternatively, one could measure the conductivity of the solution, step 25, by any means known to confirm the correct composition of the solution.

One embodiment of the counterstain, or second stain, includes reagent alcohol, eosin Y, thionin, and light or fast green SF yellowish. An acid for adjusting the pH of the counterstain solution may also be present. The reagent alcohol is 200 proof and may include about 90% ethanol, 5% isopropanol, and 5% methanol. The eosin Y, thionin, and light or fast green SF yellowish certified dye powders. The eosin Y is a fluorescent (yellow), red xanthene dye made by 2', 4', 5', 7'-tetrabrominating fluorescein. Eosin Y is certified by BSC for use as a counterstain against hematoxylin. FIG. 3 depicts the characteristics of one embodiment of the eosin Y dye used in the present invention, as available from Aldrich Chemical Company or SIGMA; however, equivalents may be used. The thionin is the same composition as used in the thionin-phenol solution. The light or fast green SF yellowish is a bluish-green, anionic triphenylmethane dye that is very soluble in water and slightly soluble in ethanol. Light or fast green SF yellowish is BSC-certified for use as a cytological counterstain. FIG. 4 depicts the characteristics of one embodiment of the light green SF yellowish dye used in the present invention, as available from Aldrich Chemical Company or SIGMA; however, equivalents may be used. The acid for adjusting the pH of the stain can be any one of most common acids, for example, acetic acid, citric acid, nitric acid, hydrochloric acid, sulfuric acid, phosphoric acid, or formic acid.

The ratio of eosin Y to solution for the counterstain is about 0.05% to about 0.1% wt/v, preferably about 0.06% to 0.08% wt/v, and more preferably about 0.0721% wt/v. The ratio for the thionin is about 0.01% to about 0.03% wt/v, preferably about 0.015% to 0.025% wt/v, and more preferably about 0.0171% wt/v. The ratio for the light or fast green SF yellowish is about 0.015% to about 0.03% wt/v and preferably about 0.0231% wt/v.

Figure 5:
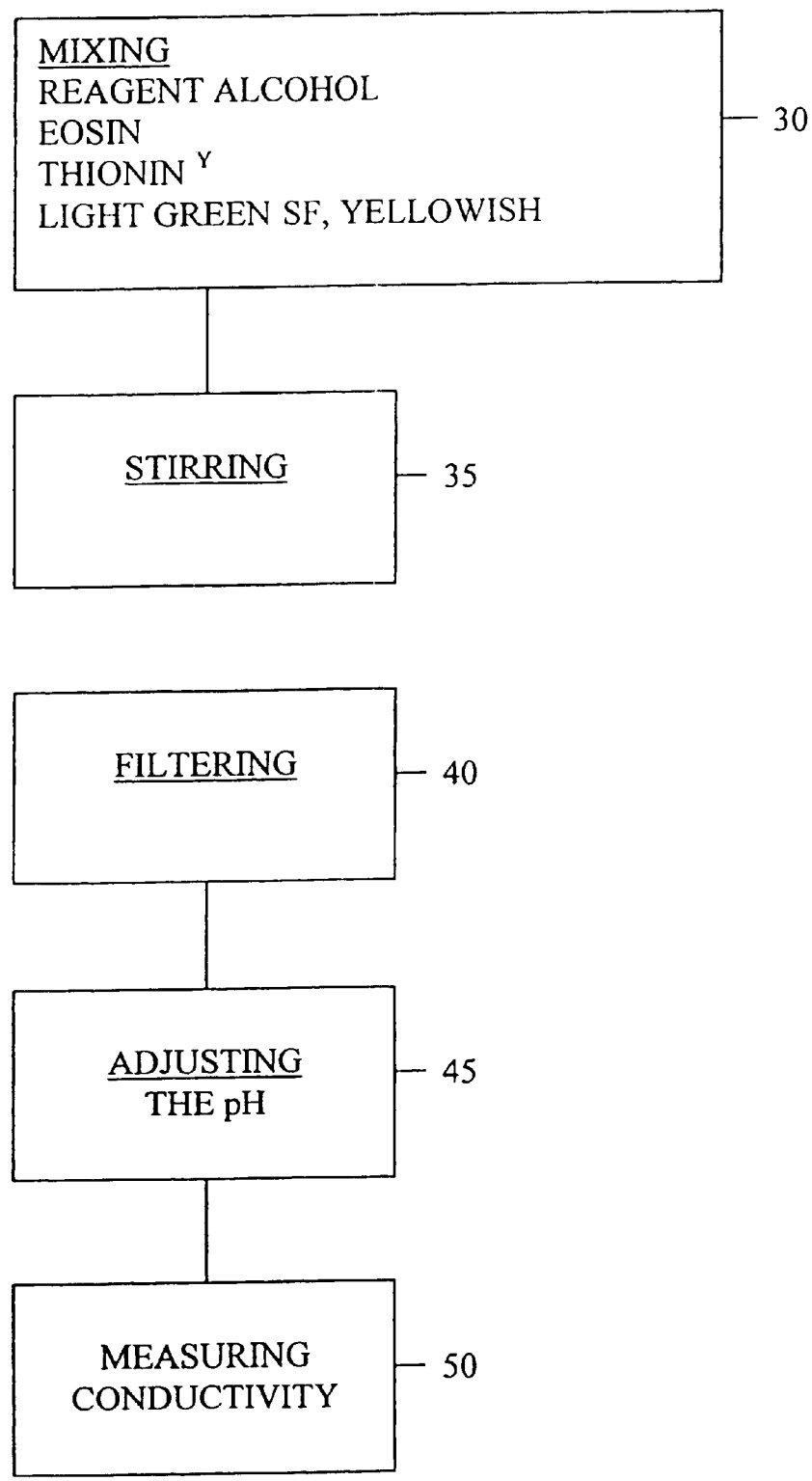
FIG. 5 is a flow chart of one method of producing a counterstain.

One method of producing the counterstain is depicted in FIG. 5. Mixing, step 30, includes adding the eosin Y, thionin, and light or fast green SF yellowish dyes to the reagent alcohol. Next, the mixture is stirred, step 35, optionally vigorously, and preferably for up to 15 hours. The mixture is then filtered, step 40. The mixture may be gravity filtered through a filter with about a 1–20 micron particle retention and preferably about 2 micron. One example is no. 4 filter paper as available from Whatmann. Finally, the pH level of the mixture is adjusted, step 45, by adding acid to the solution. The mixture may be stirred continuously while adding the acid. The pH is then adjusted to about 5 to 6 and preferably about 5.5+/−0.05. Alternatively, one could measure the conductivity of the solution, step 25, by any means known to confirm the correct composition of the solution.

A method of staining cytological material according to the invention provides improved contrast of the nucleus relative to the cytoplasm over conventional staining methods. The method produces multicolored cells suitable for manual analysis, and is also highly effective in automated analysis systems. The method entails the steps of staining the cytological material with a thionin-phenol stain, counterstaining, illuminating the stained material, and imaging the stained cytological material.

Figure 6:
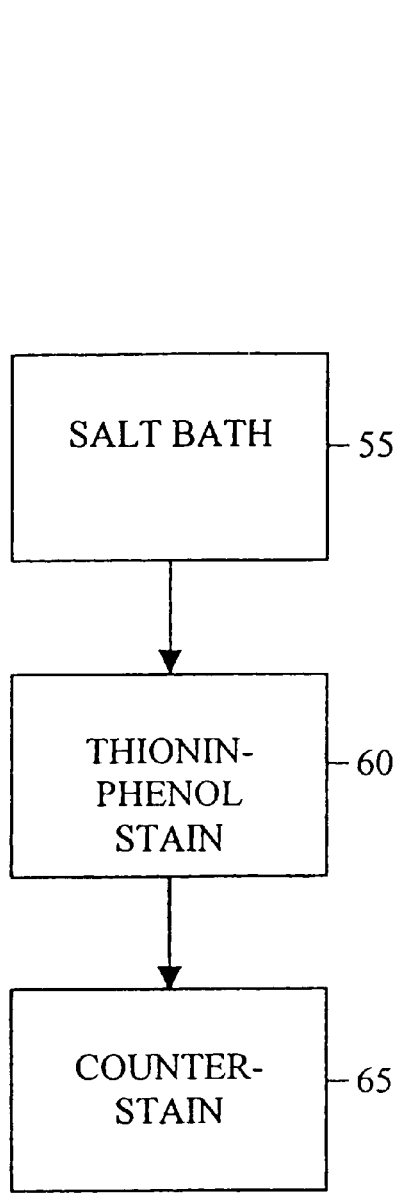
FIG. 6 is a flow chart of one method of staining a cytological material.

In one embodiment, the cells are stained by the method shown in FIG. 6. The cytological specimen is dipped or rinsed in a salt bath, step 55 of about a 10% salt solution. The solution is about 50% alcohol; wherein, the alcohol is 200 proof and consists of about 90% ethanol, about 5% isopropanol, and about 5% methanol. Step 60 entails staining the cells with a thionin-phenol stain. The stain may be about a 0.3% thionin solution. Step 65 entails counterstaining the cells with a second stain. The second stain may include thionin.

Figure 7:
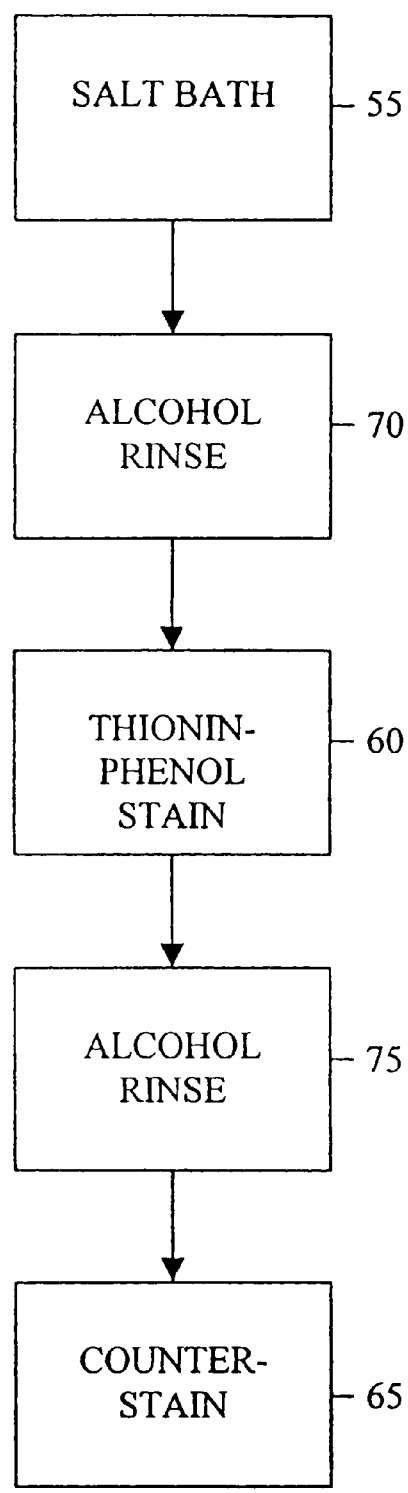
FIG. 7 is a flow chart of another method of staining a cytological material.

In another embodiment, the cells are stained by the method shown in FIG. 7. The cytological specimen is dipped or rinsed in a salt bath, step 55. Next the cells are dipped or rinsed in alcohol, step 70. Step 60 entails staining the cells with a thioninphenol stain, and step 75 entails dipping or rinsing the cells in alcohol. Lastly, step 65 counter stains the cells with a second stain.

Figure 8:
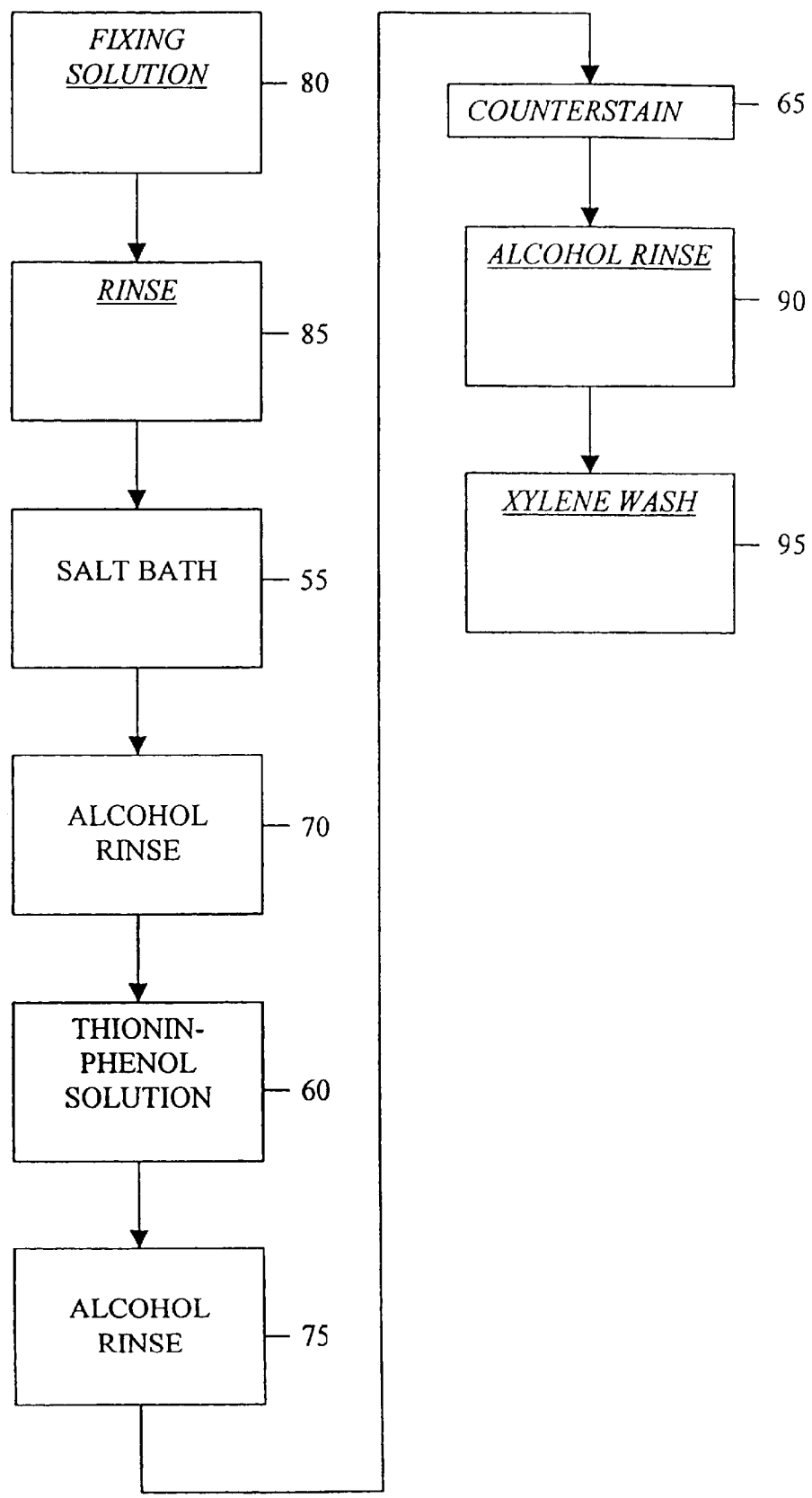
FIG. 8 is a flow chart of another method of staining a cytological material.

According to one practice of the invention, the cells are stained by the general method shown in FIG. 8. The cells are fixed on the slide, step 80, rinsed in alcohol and/or water baths, step 85, rinsed in a salt bath, step 55, rinsed in alcohol, step 70, and stained with a thionin-phenol stain solution, step 60. The stained cells are rinsed in an alcohol bath, step 75, and counterstained, step 65. After counterstaining, the stained cells are rinsed in alcohol, step 90, and rinsed in xylene or other commercially available xylene substitutes, step 95.

Figure 9:
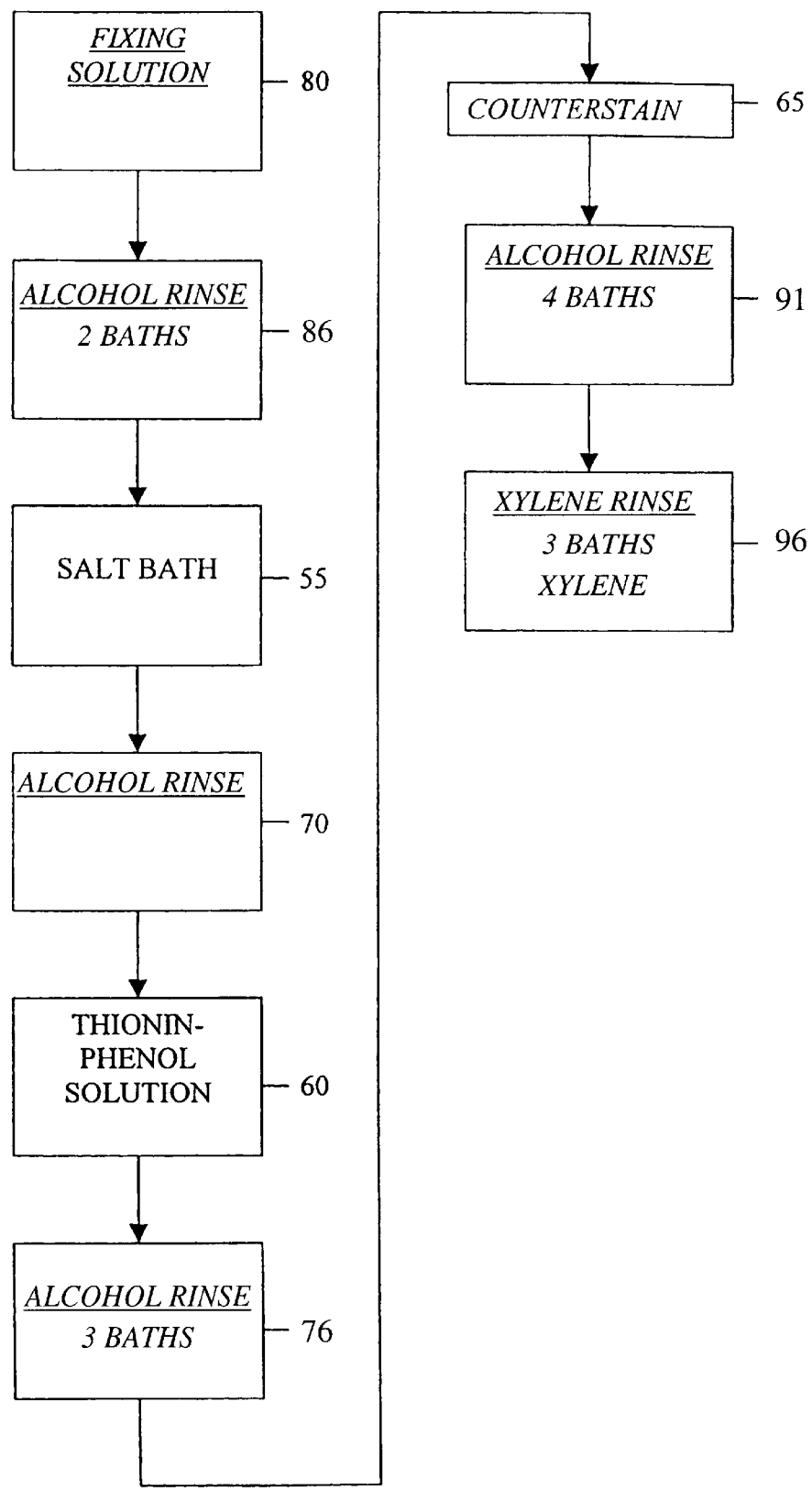
FIG. 9 is a flow chart of another method of staining a cytological material.

As shown in FIG. 9, the cells are first fixed on a slide using alcohol and wax, or other method known in the art, step 80. Then, in preparation for staining, the slide is dipped ten to twenty times in each of two baths, where one is a high percentage, low molecular weight alcohol, preferably ethanol, and the other is an alcohol bath or a water bath, step 86. Next, the cells are dipped in a salt bath for about five to about fifteen minutes, generally for about ten minutes, step 55, after which the cells are rinsed in an alcohol bath, step 70. The cells are then stained in a thionin-phenol stain solution, step 60, for a time sufficient to incorporate the thionin dye in the nuclei, which may range from three minutes to about thirty minutes, but is typically about ten minutes. Those skilled in the art will recognize that the staining time can be determined by taking several factors into account, including the desired intensity of the stain appropriate for the cell type and the viewing system used. Automated imaging systems generally require darker staining than human visual evaluation, and certain types of cells stain faster than others. Also, the amount of thionin in the stain can affect the staining time. Lower concentrations of thionin will generally require longer staining times. A thionin stain useful for most cells is slightly acidic, typically having a pH of about 6.7.

After rinsing by dipping ten to twenty times in each of two to three high percentage, low molecular weight alcohol baths, followed by a third bath lasting approximately five minutes in a high percentage, low molecular weight alcohol, step 76, the cells are counterstained, step 65, for a time sufficient to incorporate the dye in the cytoplasm and nuclei, which may range from about two minutes to about thirty minutes, but is generally about four minutes. Those skilled in the art will recognize that the staining time may vary, as discussed hereinabove. The counterstain also includes thionin in an amount sufficient to replenish the thionin that may have been depleted during the dipping and rinsing steps, and is selected to absorb light at a different wavelength from the thionin-stained nuclear material. After staining and counterstaining, the slide is rinsed by dipping in two to four more high percentage, low molecular weight alcohol baths, step 91, and two or more xylene rinses or other commercially available xylene substitutes, step 96. The cells are now ready to be analyzed.

When viewed under visible light, the nuclei of the cells are transparent to opaque and stained a deep blue. The cytoplasm is transparent and is multicolored, with the specific color pattern depending on the counterstain used. When cells are stained in this manner, the color pattern is familiar to cytologists, so analysis can readily be carried out by manual, i.e., human vision. The method has the added advantage in that, when viewed by an imaging system, each nucleus is opaque and the cytoplasm is nearly invisible resulting in very high contrast between nuclear and cytoplasmic material and thereby providing high resolution. With the cytoplasm nearly invisible, overlapping cells will not be confused with nuclei, and an accurate cell count can be achieved readily, manually or by computer.

Figure 10:
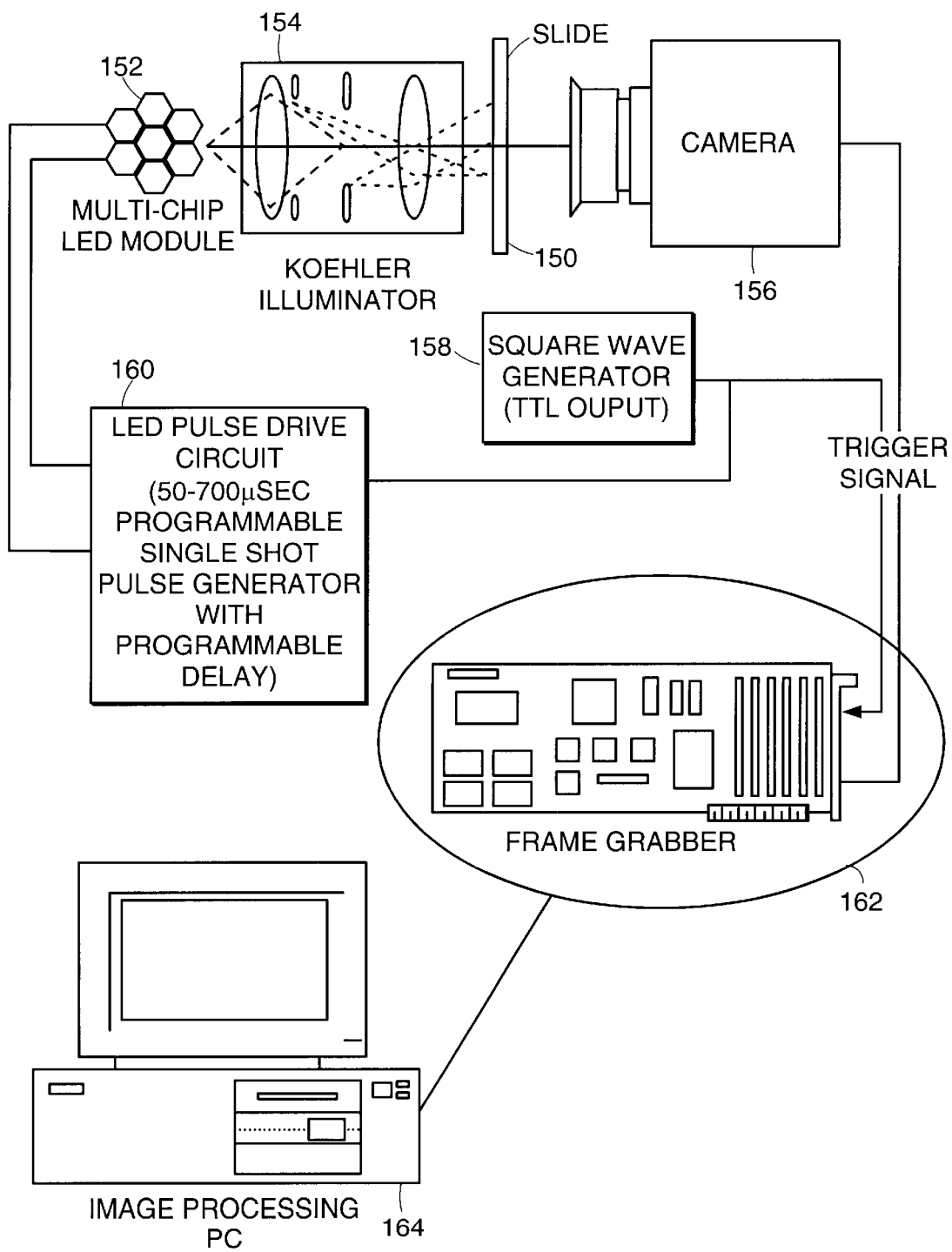
FIG. 10 is a schematic of an LED fiber illumination system.
Figure 11:
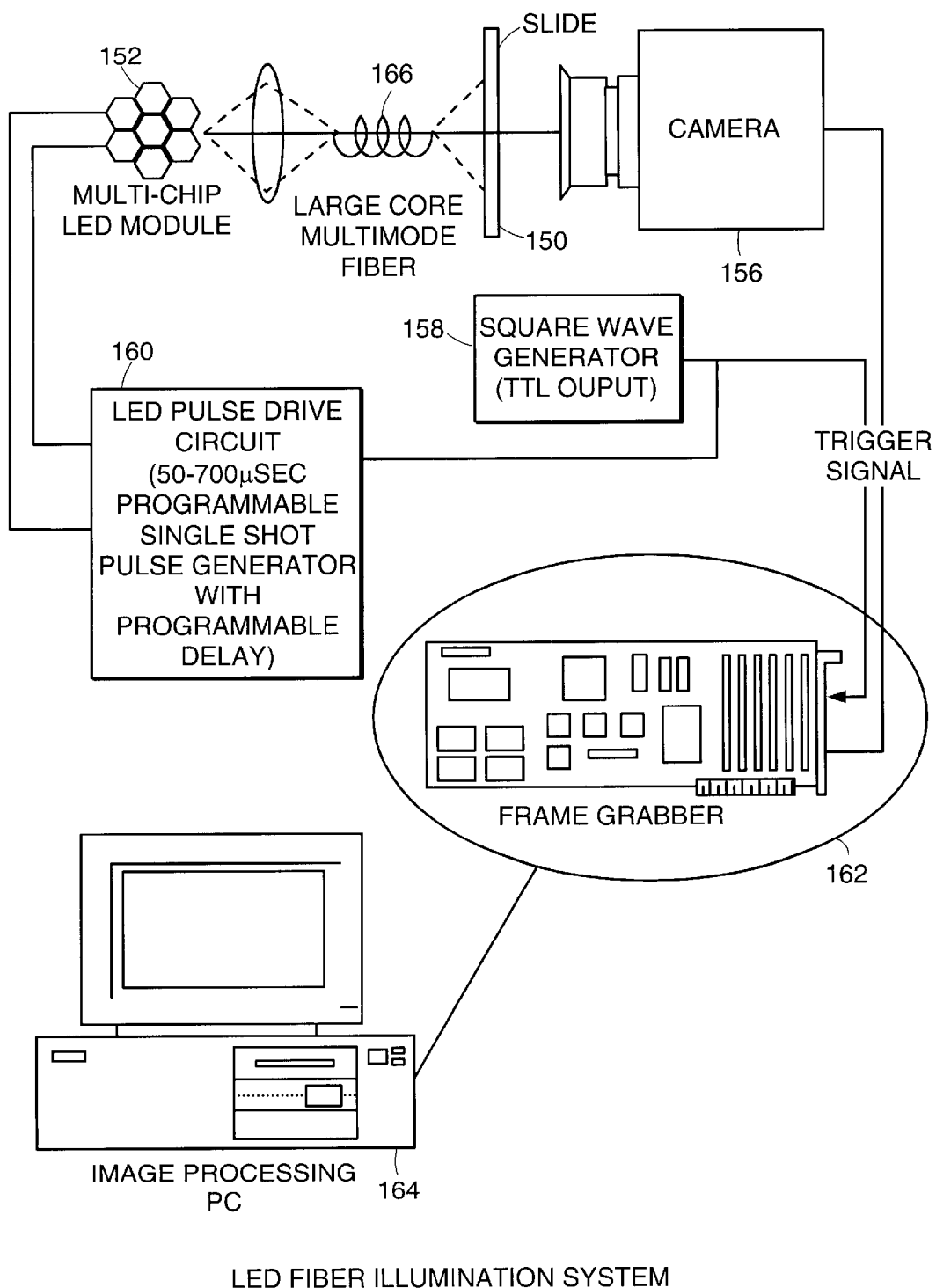
FIG. 11 is a schematic of an LED Koehler illumination system.

Referring now to FIGS. 10 and 11, one purpose of an optical instrument lighting system in accordance with the present invention is to provide high intensity narrow band light for imaging a cytological specimen on a microscope slide 150. This purpose is implemented using high brightness LEDs in either a single discrete LED, combination of single discrete LEDs, or custom multi-chip LED module configuration 152. LEDs generate a small amount of heat, which restricts the amount of current at which they can be driven before output wavelengths shift, consequently, restricting the amount of light which these devices emit. To increase the light output from the device, the LEDs may be driven with a pulse circuit 160 that is synchronized with a camera 156 of the imaging system 164 to deliver short, intense pulses of light to the camera during the camera integration period.

The LED pulse is synchronized with the camera frame integration by providing a external trigger that triggers both the camera/frame grabber 162 and the LED pulse driver 160, for example using a square wave generator 158. The camera 156 does not respond instantaneously to the trigger. To compensate for this delay, the pulse drive circuit 160 has a programmable delay that is used to synchronize the systems. Other synchronization methods are possible, depending on the camera type and actual implementation.

LEDs inherently produce spatially nonuniform light output and some machine vision imaging applications require reasonably uniform illumination of the sample. For situations where uniformity is an issue, two types of systems for generating spatially uniform illumination may be used with LEDs, namely, Koehler and fiber optic systems. The LEDs used in either of these systems may be discrete LEDs packaged in close proximity or multiple LED dies may be integrated on a single substrate to produce a more dense arrangement.

Koehler illumination (see FIG. 10) is a standard technique for producing uniform illumination of a microscope slide 150 from the spatially nonuniform filament of an incandescent lamp used in traditional microscope illuminators. As determined by testing, this technique is equally effective at achieving uniformity when employed with LED sources. In this embodiment of the LED illuminator, individual LEDs are packaged closely together and placed in the general position of the lamp filament in the traditional Koehler illuminator 154 and positioned for Koehler illumination.

In another embodiment for achieving uniformity, multiple LEDs are coupled into a large core (=500 to 600 $\mu$m) optical fiber 166 with lenses or other optical apparatus, See FIG. 11. The length of the fiber is selected so that the spatial nonuniformities of the LEDs are mixed together and a relatively uniform spatial output from the fiber 166 is achieved. In practice, the output of the fiber 166 is approximately Gaussian in spatial profile. The fiber 166 may have to be displaced from the microscope slide 150, such that only the central, relatively flat, portion of the output is used.

Figure 12:
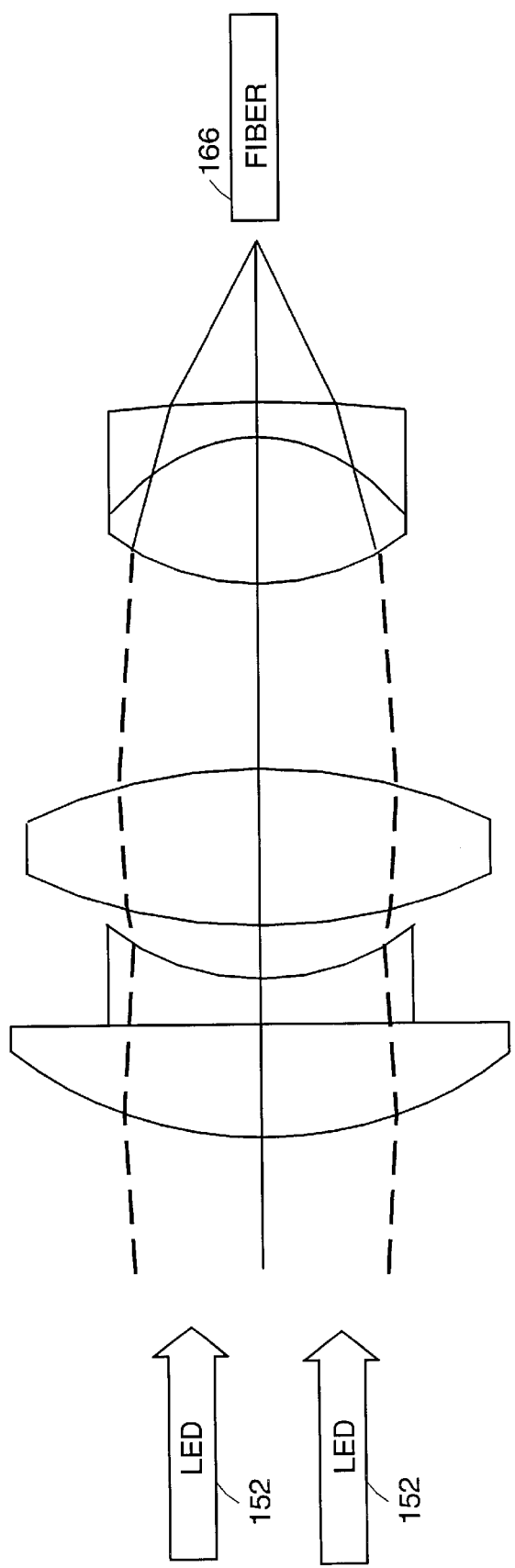
FIG. 12 is a schematic of an optics system to couple two LEDs to a fiber optic cable.

Consider the case where the multi-chip LED module 152 contains two LEDs. Two discrete LEDs having a full-angle divergence of 8 degrees are placed side-by-side such that both emitters fall within a 4 mm diameter. The lenses collect the light and image both emitters onto the 600 $\mu$m core of the fiber 160. See FIG. 12. The package diameter of individual LEDs is typically on the order of 3–5 mm. Thus, it may be necessary to remove some of the nonessential plastic packaging on a standard LED in order to get the two emitters side-by-side within 4 mm.

Figure 13A:
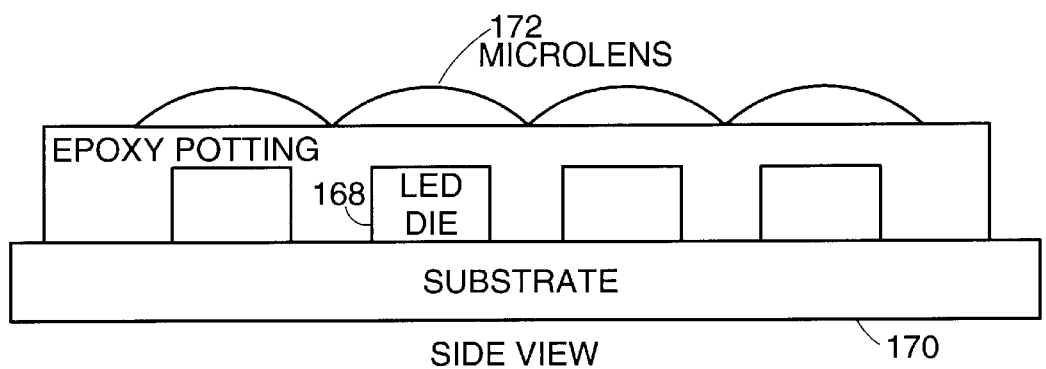
FIG. 13A is a schematic top view of an LED multichip module.
Figure 13B:
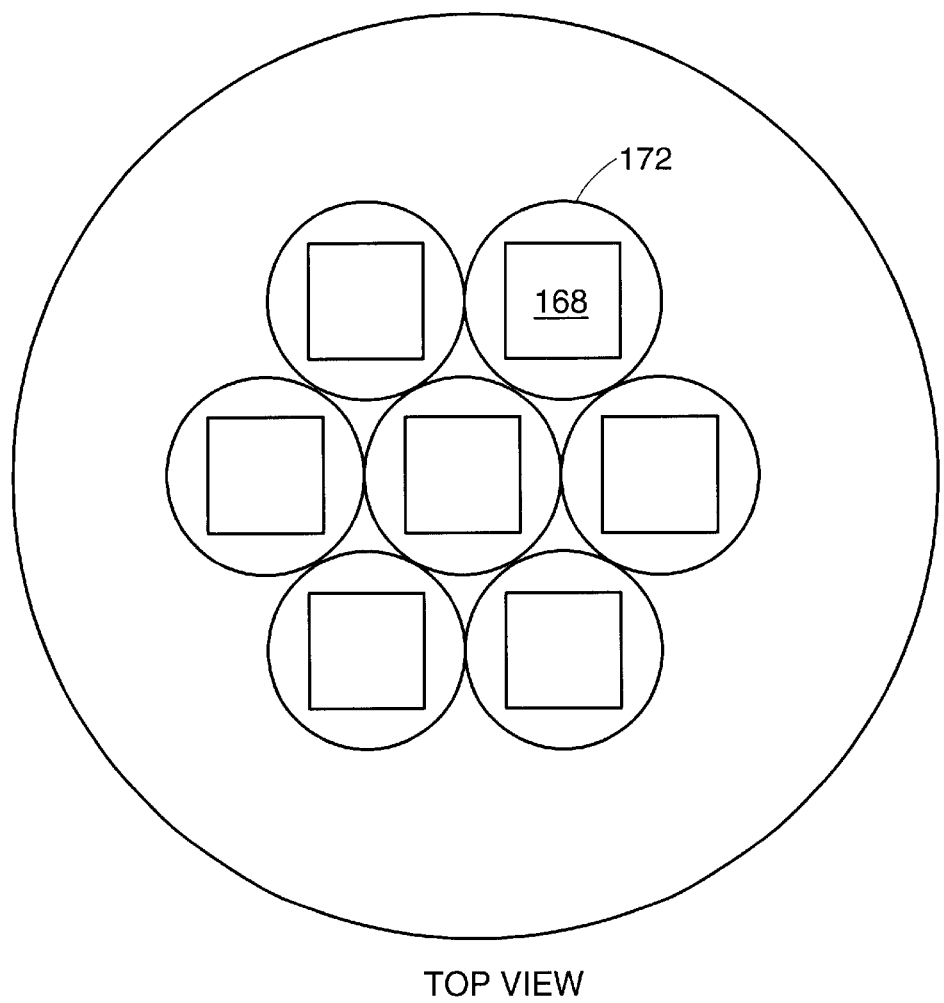
FIG. 13B is a schematic side view of an LED multichip module.

As an alternative to individual LEDs, multiple LED dies 168 may be placed on a single substrate 170 See FIGS. 13A and 13B. Individual lenses 172 can be placed above each die 168 so that the radiation from each die 168 is collected into a narrow cone, rather than being spread into 2π steradians. Microlenses with diameters of about 1 mm are commercially available. A hexagonal pattern of 1 mm lenses could pack about twelve LED die 168 onto a single substrate 170 with a diameter of about 4 mm. A substrate 170, such as one with high thermal conductivity, may be used to hold multiple LED dies 168. Conductive patterns on the substrate 170 are used to wire bond the dies 168 to the substrate 170 for electrical connections. The dies 168 are potted in a polymer, for example an epoxy, for protection from moisture and other elements. The individual microlenses 172 are placed on top to provide collection of the light into a narrow cone.

An extension of this concept consists of combining different wavelength LEDs to produce a light source which emits multiple narrow wavelength bands. This technique provides a method to illuminate objects such as cytological specimens on microscope slides at multiple wavelengths simultaneously. Further, the output bands can be tailored to the application by selection of appropriate LEDs. The energy from each band can be tailored to the application by employing separate drive systems, pulsed or continuous as required, for each wavelength.

In one embodiment, a cluster or array of seven LEDs replaces the standard incandescent microscope illumination. The LEDs are oriented in the configuration shown in FIG. 14A. Different spatial orientations may be used to obtain two colors. One, shown in FIG. 14B, provides for two triplets of LEDs where "X" represents one color LED and "O" represents another. Two wavelengths are selected, one allowing optimal nuclear detection among red cytoplasm and the other allowing optimal nuclear detection among green cytoplasm. The second orientation as shown in FIG. 14C allows for nine LEDs, with four illuminating one color and five illuminating the other color. In additional embodiments, the LED array may include essentially any combination of the two different color LEDs, such as one red LED and eight green LEDs. Choices of the color and number of LEDs depends on desired brightness, camera response at the selected wavelengths, and availability of LEDs with specific emission angles, for example, 35 degree and 65 degree emission angle LEDs. Typical angles range from about 24 to about 72 degrees. The red LEDs are used for exposing the stained cytological material to a light source having a wavelength of about 690 nm to about 750 nm to determine that a specific stain was used. The green LEDs having a wavelength of about 500 nm to about 600 nm are used to illuminate the cytological material for imaging. Multiple green LEDs are desirable, because increased imaging response times can be achieved with the increased illumination.

Figure 15:
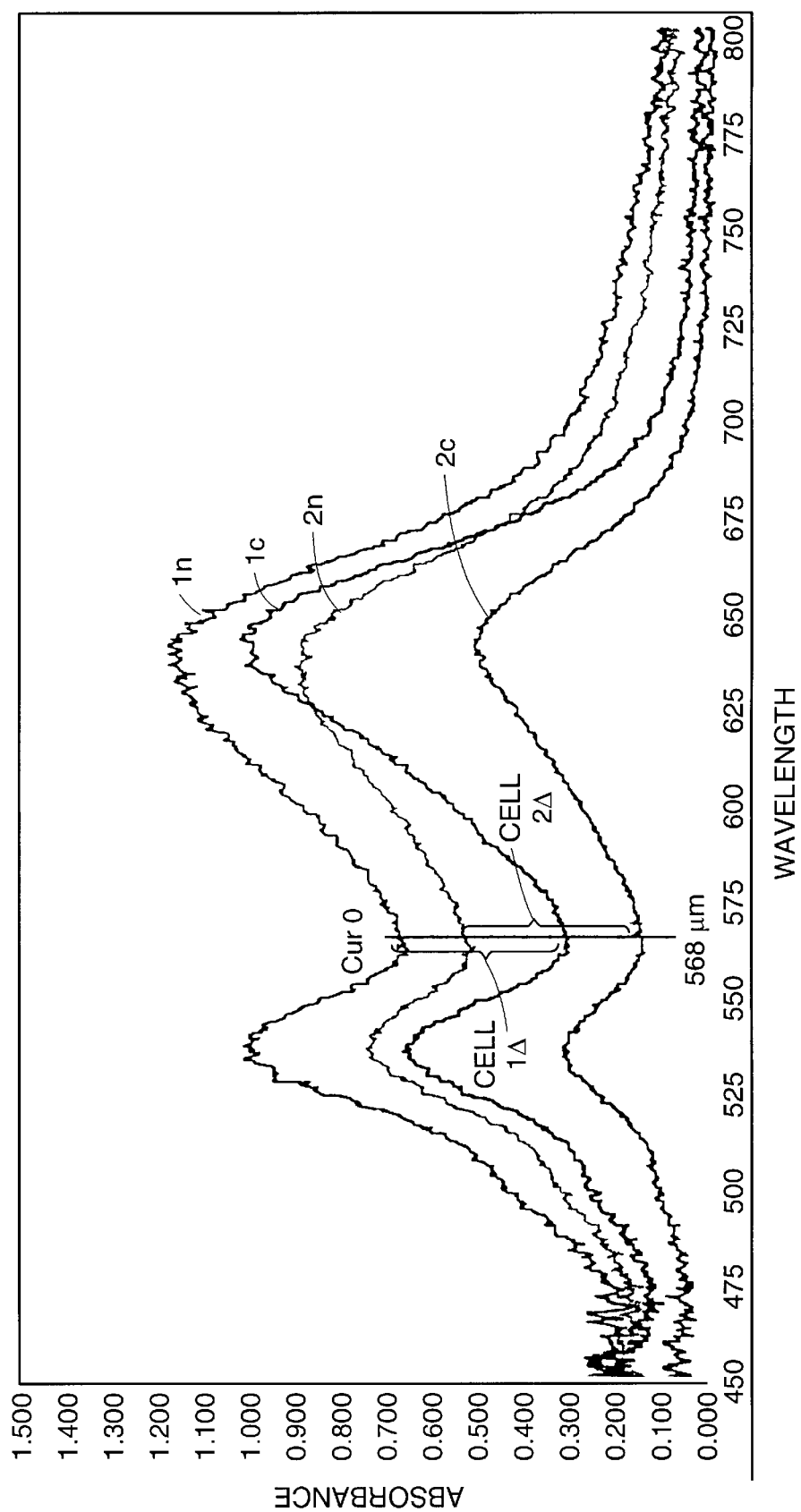
FIG. 15 is a graph depicting an example of the absorption spectra of the individual components of the stain in solution.
Figure 16:
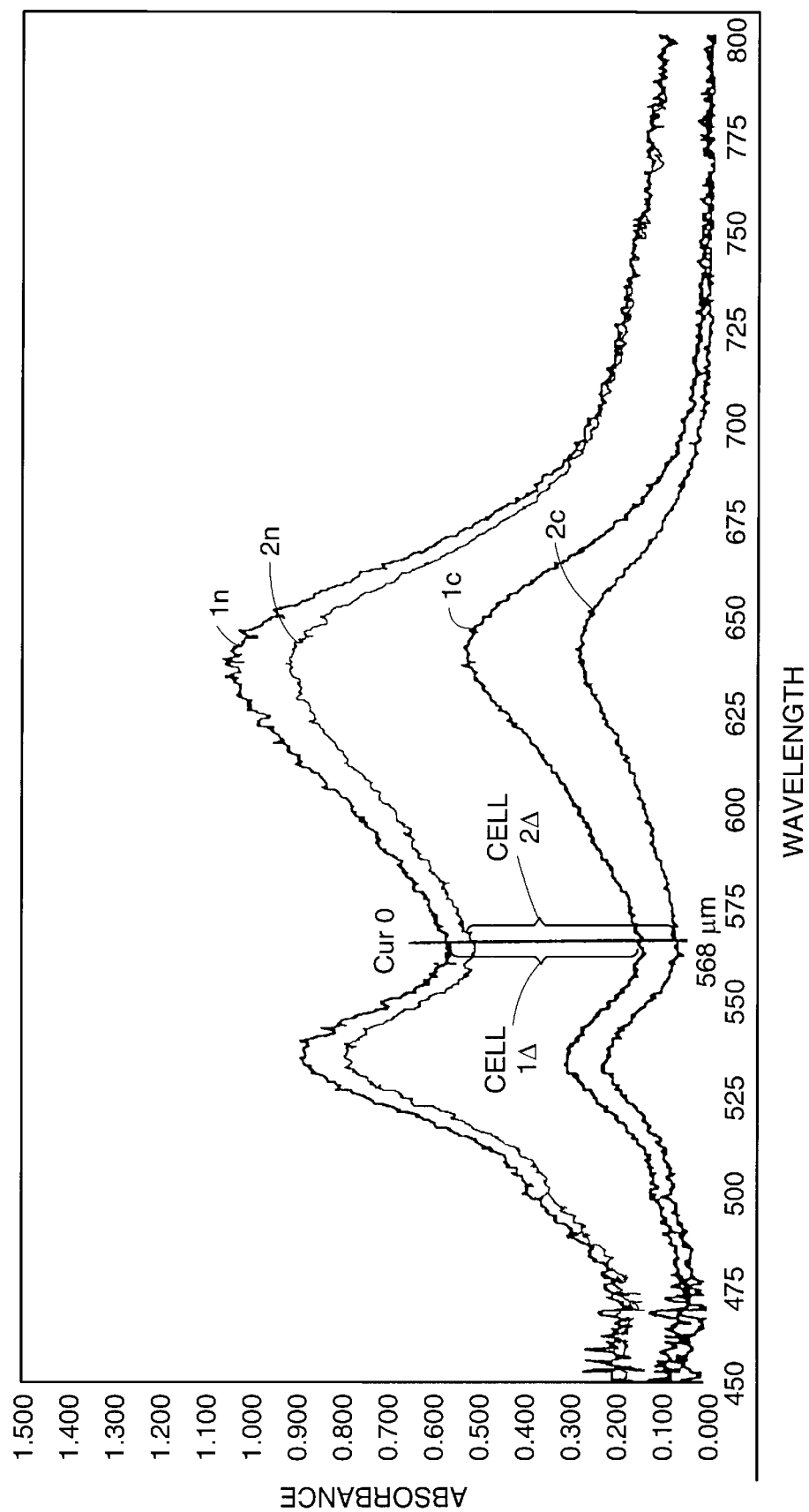
FIG. 16 is a graph depicting another example of the absorption spectra of the individual components of the stain in solution.
Figure 17:
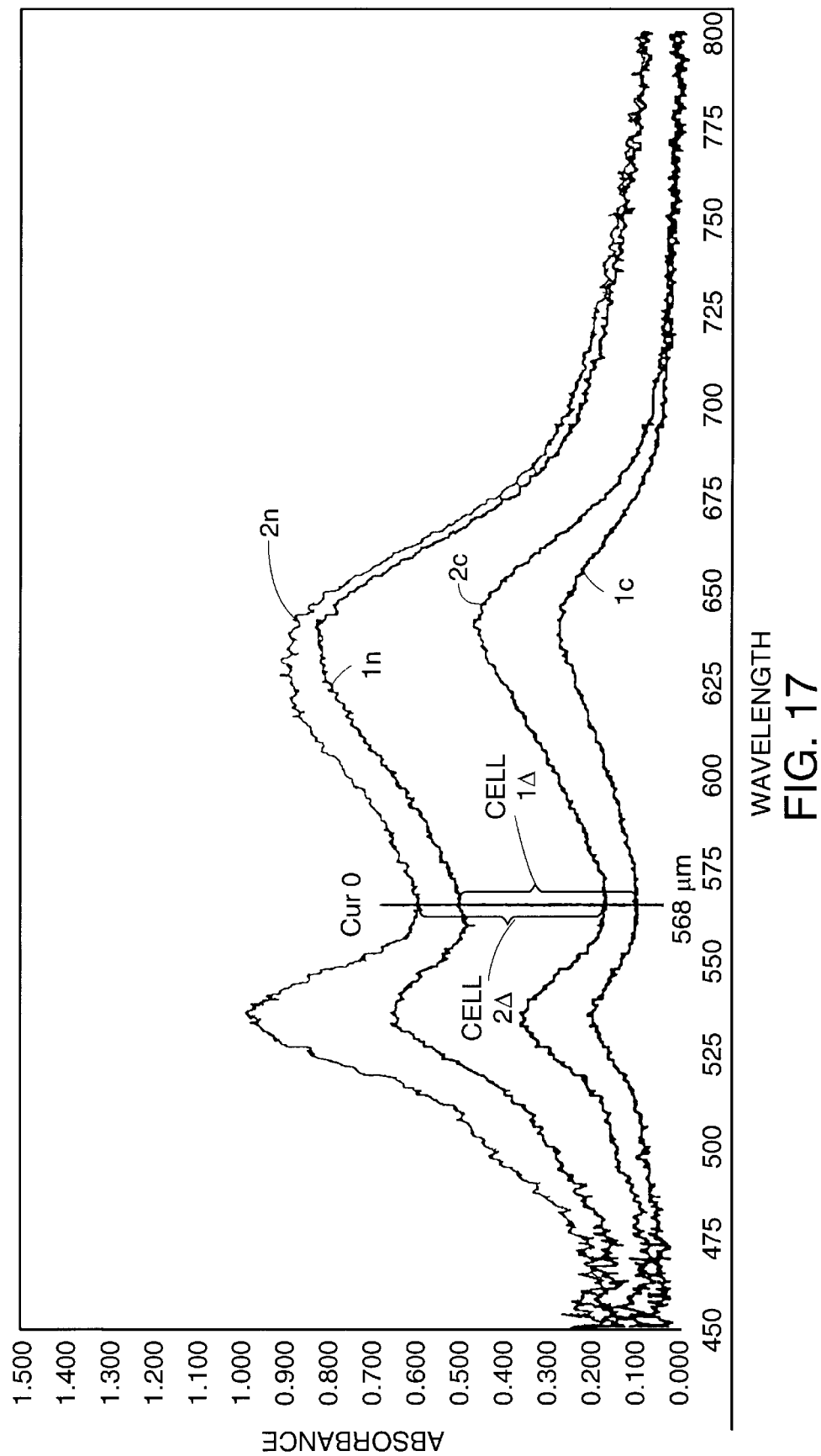
FIG. 17 is a graph depicting yet another example of the absorption spectra of the individual components of the stain in solution.

FIGS. 15–17 depict various examples of the absorption spectra of the individual components of the stains in solution. Two peaks are readily apparent from the graphs. One peak is associated with red light and the other is associated with green light. It is generally desirable to image the cytological material at a wavelength at which green and red light is minimally transmitted, i.e., the valley formed between the two spectral peaks, in this instance about 568 nm.

Figure 18:
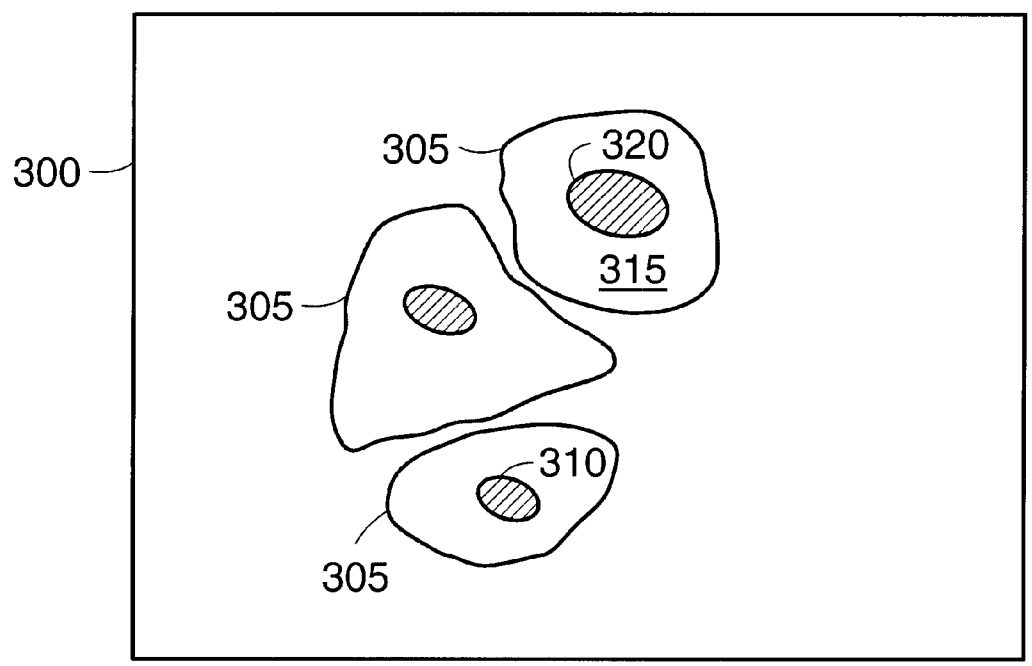
FIG. 18 is a schematic representation of cytological material.

FIG. 18 is a schematic representation of cytological material as it may be seen on a typical slide 300. Each cell 305 consists of a nucleus 310 and cytoplasm 315. A representative abnormal nucleus 320 is also shown.

Figure 19:
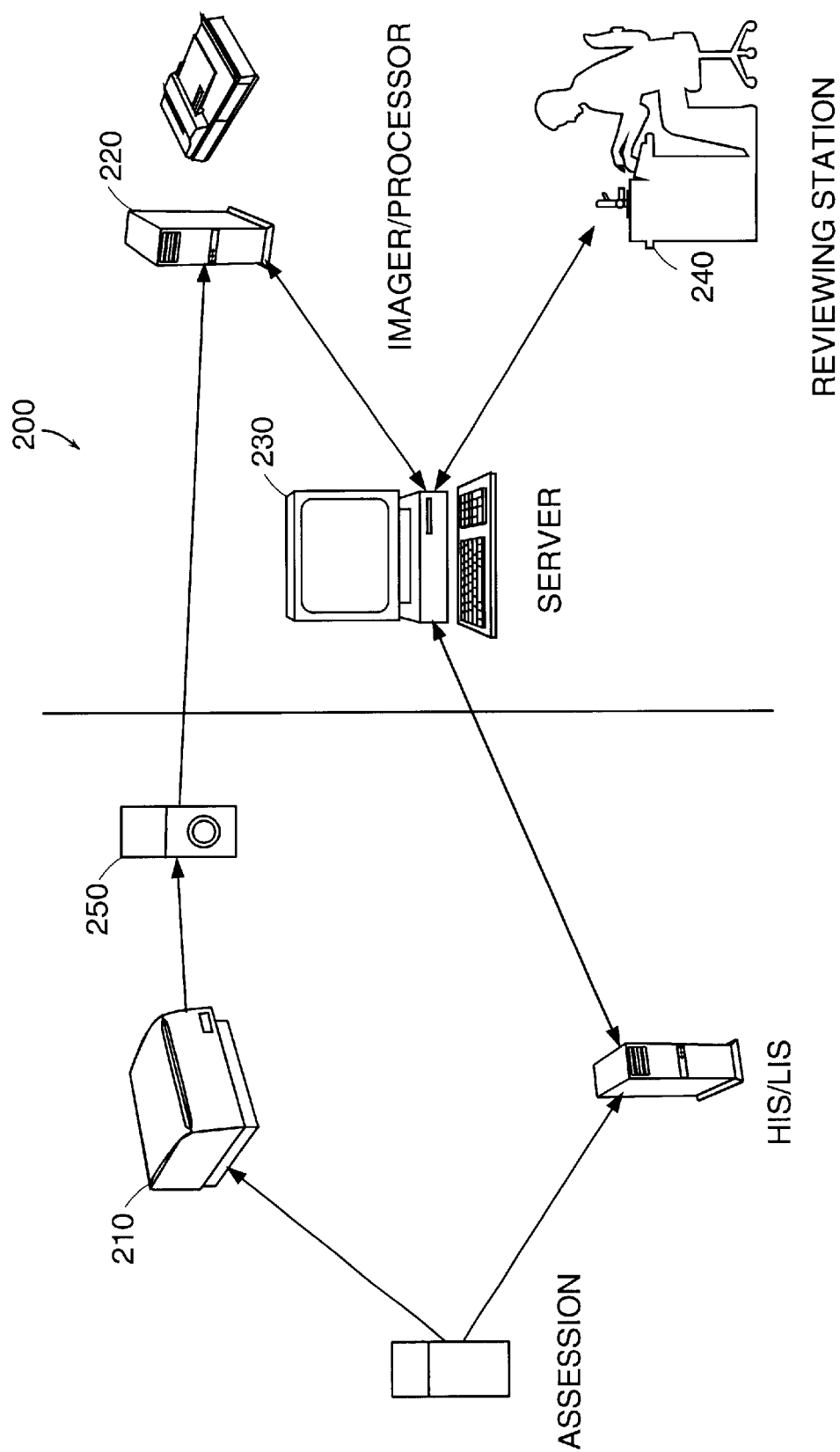
FIG. 19 is a schematic representation of an imaging system and cooperating components in a laboratory setting.

FIG. 19 is a schematic representation of an imaging system and related components in a laboratory setting. The overall system 200 may include a system 210 for preparing slides 150 with cytological material for review, an imager/processor 220 for imaging the cytological material and processing the pertinent data, a compute server 230 for storing and/or further processing the data, and a reviewing station 240 for manually reviewing the slides based on data collected by the imager 220.

Having described certain preferred and exemplary embodiments of the invention, it will be apparent to those of ordinary skill in the art that other embodiments incorporating the concepts disclosed herein can be used without departing from the spirit and the scope of the invention. The described embodiments are to be considered in all respects only as illustrative and not limiting. Therefore, it is intended that the scope of the present invention be only limited by the following claims.

What is claimed is:

1. A cytological staining solution, comprising:
   methanol;
   phenol; and
   thionin.

2. The staining solution of claim 1, wherein the methanol is various grades.

3. The staining solution of claim 1, wherein the phenol comprises loose crystals with a purity of at least about 95%.

4. The staining solution of claim 1, wherein the thionin comprises a certified dye powder.

5. The staining solution of claim 1 further comprising an acid, wherein the acid is chosen from the group consisting of acetic acid, phosphoric acid, nitric acid, formic acid, citric acid, sulfuric acid, and hydrochloric acid.

6. The staining solution of claim 1, wherein the acid is glacial acetic acid.

7. The staining solution of claim 1, wherein the pH of the staining solution is acidic.

8. The staining solution of claim 1, wherein the pH is between about 5 to about 7.

9. The staining solution of claim 1, wherein the staining solution has a pH of about 6.7+/−0.05.

10. The staining solution of claim 1, wherein the phenol has a weight to volume ratio of about 0.8% to about 1.2%.

11. The staining solution of claim 1, wherein the phenol has a weight to volume ratio of about 1%.

12. The staining solution of claim 1, wherein the thionin is synthesized.

13. The staining solution of claim 1, wherein the thionin has a weight to volume ratio of about 0.2% to about 0.4%.

14. The staining solution of claim 1, wherein the thionin has a weight to volume ratio of about 0.3%.

15. The staining solution of claim 1, wherein the thionin has a weight to volume ratio of about 0.345%.

16. A method of producing a cytological staining solution, the method comprising the steps of:
   mixing methanol, phenol, and thionin;
   stirring the mixture;
   filtering the mixture; and
   adjusting the pH of the mixture to a value of about 6.7 by adding an acid thereto to produce the staining solution.

17. The method of claim 16, wherein the acid is chosen from the group consisting of acetic acid, phosphoric acid, nitric acid, formic acid, citric acid, sulfuric acid, and hydrochloric acid.

18. The method of claim 16, wherein the acid is glacial acetic acid.

19. The method of claim 16, wherein the mixture is mixed for at least about 1 hour.

20. The method of claim 16, further comprising the step of mixing the mixture while adding the acid.

21. The method of claim 16, wherein the mixing step comprises mixing an equivalent ratio of about one liter of methanol, about 10 grams of phenol, and about 3.45 grams of thionin.

22. The method of claim 16, wherein the filtering step utilizes a filter with about 1–20 micron particle retention.

23. A cytological counterstaining solution, comprising:
reagent alcohol;
eosin Y;
thionin; and
light or fast green SF yellowish.

24. The counterstaining solution of claim 23, wherein the reagent alcohol is 200 proof.

25. The counterstaining solution of claim 23 further comprising an acid, wherein the reagent alcohol comprises about 90% ethanol, about 5% isopropanol, and about 5% methanol.

26. The counterstaining solution of claim 23, wherein the eosin Y comprises a certified dye powder.

27. The counterstaining solution of claim 23, wherein the thionin comprises a certified dye powder.

28. The counterstaining solution of claim 23, wherein the light or fast green SF yellowish comprises a certified dye powder.

29. The counterstaining solution of claim 23, further comprising an acid, wherein the acid is chosen from the group consisting of acetic acid, phosphoric acid, nitric acid, formic acid, citric acid, sulfuric acid, and hydrochloric acid.

30. The counterstaining solution of claim 23, wherein the acid is glacial acetic acid.

31. The counterstaining solution of claim 23, wherein the pH of the counterstaining solution is acidic.

32. The counterstaining solution of claim 23, wherein the pH of the counterstaining solution is about 5 to about 6.

33. The counterstaining solution of claim 23, wherein the counterstaining solution has a pH of about 5.5+/-0.05.

34. The counterstaining solution of claim 23, wherein the eosin Y has a weight to volume ratio of about 0.05% to about 0.1%.

35. The counterstaining solution of claim 23, wherein the eosin Y has a weight to volume ratio of about 0.721%.

36. The counterstaining solution of claim 23, wherein the thionin has a weight to volume ratio of about 0.01% to about 0.03%.

37. The counterstaining solution of claim 23, wherein the thionin has a weight to volume ratio of about 0.0171%.

38. The counterstaining solution of claim 23, wherein the light or fast green SF yellowish has a weight to volume ratio of about 0.015% to about 0.03% for the light green and about 0.005% to about 0.01% for the fast green.

39. A method of producing a cytological counterstaining solution, the method comprising the steps of:
mixing reagent alcohol, eosin Y, thionin, and light or fast green SF yellowish;
stirring the mixture;
filtering the mixture; and
adjusting the pH of the mixture to a value of about 5.5 by adding an acid thereto to produce the counterstaining solution.

40. The method of claim 39, wherein the acid is chosen from the group consisting of acetic acid, phosphoric acid, nitric acid, formic acid, citric acid, sulfuric acid, and hydrochloric acid.

41. The method of claim 39, wherein the acid is glacial acetic acid.

42. The method of claim 39, wherein the mixture is mixed for at least about 1 hour.

43. The method of claim 39, further comprising the step of mixing the mixture while adding the acid.

44. The method of claim 40, wherein the mixing step comprises mixing an equivalent ratio of about one liter of reagent alcohol, about 0.721 grams of eosin Y, about 0.171 grams of thionin, and about 0.231 grams of light green SF yellowish or about 0.065 grams of fast green SF yellowish.

45. The method of claim 39, wherein the filtering step utilizes a filter with about 1–20 micron particle retention.

46. A method of staining cytological material, the method comprising staining the cytological material with a thionin-phenol solution.

47. The method of claim 46, further comprising the step of rinsing the cytological material in a salt bath prior to staining.

48. The method of claim 46, further comprising the step of counterstaining the cytological material with a second stain.

49. The method of claim 46, wherein the salt bath is about a 10% salt solution.

50. The method of claim 46, wherein the thionin-phenol solution is about a 0.3% thionin solution.

51. The method of claim 46, wherein the thionin-phenol solution comprises methanol, phenol, and thionin.

52. The method of claim 46, wherein the thionin is synthesized.

53. The method of claim 48, wherein the second stain comprises reagent alcohol, eosin Y, thionin, and light or fast green SF yellowish.

54. The method of claim 46, wherein the thionin-phenol solution binds preferentially to nuclear cytological material relative to cytoplasmic cytological material.

55. The method of claim 48, wherein the second stain binds preferentially to cytoplasmic cytology material relative to nuclear cytological material.

56. The method of claim 48, wherein at least one of the thionin-phenol solution and the second stain discernibly stain the cytological material in a visible light range.

57. The method of claim 48, wherein both the thionin-phenol solution and the second stain discernibly stain the cytological material in a visible light range.

58. The method of claim 46, further comprising the step of rinsing the cytological material after staining the cytological material.

59. The method of claim 48, wherein the second stain contains thionin to retard thionin depletion during the rinsing step.

60. The method of claim 52, wherein the cytological material is rinsed in an alcohol bath.

61. A method of counterstaining a cytological sample, the method comprising counterstaining the cytological sample with a stain that includes a component of the previous stain, wherein the component of the stain retards the component depletion during the rinsing step.

62. The method of claim 61, further comprising the step of rinsing the cytological sample prior to counterstaining.

* * * * *